United States Patent [19]

Amato et al.

[11] Patent Number: 4,883,878

[45] Date of Patent: Nov. 28, 1989

[54] PROCESS FOR UNSYMMETRICAL DITHIOACETALS AND DITHIOKETALS

[75] Inventors: Joseph S. Amato, Brooklyn, N.Y.; James M. McNamara, Rahway, N.J.; Johnnie L. Leazer, Jr., Piscataway, N.J.; Paul J. Reider, Westfield, N.J.; Robert A. Reamer, Bloomfield, N.J.

[73] Assignee: Merck & Co. Inc., Rahway, N.J.

[21] Appl. No.: 153,399

[22] Filed: Feb. 8, 1988

[51] Int. Cl.$^4$ .................................. C07D 215/12
[52] U.S. Cl. ................................ 546/172; 546/14; 546/175
[58] Field of Search .................... 546/175, 172, 14

[56] References Cited

PUBLICATIONS

C. D. Perchonock et al., "Synthesis and Structure Activity Relationship Studies of a Series of 5-Aryl-4,6-dithianonanedioc Acids . . . ", J. Med. Chem., 29; 1442–1452 (1986).

D. A. Evans et al., "Thiosilanes, a Promising Class of Reagents for Selective Carbonyl Protection", J. Am. Che. Soc., 99, 5009–5017 (1977).

C. M. Leir, "An Improvement in the Doebner–Miller Synthesis of Quinaldines", J. Org. Chem., 42, 911–913 (1977).

*Primary Examiner*—David B. Springer
*Attorney, Agent, or Firm*—Richard S. Parr; Michael C. Sudol

[57] ABSTRACT

This invention relates to a novel process for preparing unsymmetrical dithioacetals and dithioketals from aryl aldehydes and ketones.

6 Claims, No Drawings

PROCESS FOR UNSYMMETRICAL DITHIOACETALS AND DITHIOKETALS

BACKGROUND OF THE INVENTION

This invention relates to a novel process for preparing unsymmetrical dithioacetals and dithioketals from aryl aldehydes and ketones. More particularly, this invention relates to a process for preparing certain 2-substituted quinoline dithiaalkanedioic acids.

Various methods for preparing dithioacetals and dithioketals from aldehyde or ketone precursors are well known in the art, especially where the two thioether moieties are identical or are constituent parts of a cyclic functionality. For example, reaction of thiol or activated thiol reagents with carbonyl-containing or activated carbonyl-containing reagents can yield symmetric and cyclic dithioacetals and dithioketals. Activation by addition of a suitable Lewis acid or a trialkylsilyl halide has been reported. Thus, certain symmetric and cyclic dithioacetals have been prepared by reaction of mercaptans and aldehydes (or corresponding dimethyl acetals) in the presence of boron trifluoride etherate. C. D. Perchonock et al., *J. Med. Chem.*, 29, 1442–1452 (1986). However, preparation of unsymmetric dithioacetals and dithioketals presents special synthetic problems. Using a mixture of two different thiols in the aforementioned reaction produces the unsymmetrical product, but only as one component in a statistical mixture of symmetrical and unsymmetrical products.

One method for preparing unsymmetrical dithioacetals and dithioketals involves modifying existing symmetrical dithioacetals and dithioketals, e.g., copending U.S. patent application Ser. No. 011,181, filed Feb. 5, 1987. Since selective modification of only one of the two identical thioether moieties would rarely be efficient, one would expect this method to have only limited applicability.

Selective methods for preparing hemithioacetals have been reported. For example, reactions of various aldehydes and ketones with alkyl- and arylthiosilanes of the formula $RSSi(CH_3)_3$ have been reported to yield, depending upon the specific conditions used, O-silyl-hemithioacetals and ketals of

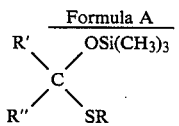

Formula A or dithioacetals and dithioketals of Formula B

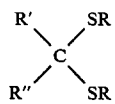

wherein R is inter alia alkyl, alkylene (forming a cyclic dithioketal), or other saturated or unsaturated hydrocarbon species; and wherein for aldehydes one of R' and R" is hydrogen and the other is inter alia alkyl or other saturated or unsaturated hydrocarbon species, and for ketones R' and R" are independently inter alia alkyl, alkylene (derived from cyclic ketones), or other saturated or unsaturated hydrocarbon species. D. A. Evans et al., *J. Am. Chem. Soc.*, 99, 5009–5017 (1977). However, no practical method has been reported for selective preparation of unsymmetrical dithioacetals. For example, the method described by Evans has not been found useful for the preparation of the 2-substituted quinoline dithiaalkanedioic acids described in this invention.

A method described in copending U.S. patent application Ser. No. 011,166, filed Feb. 5, 1987, for preparing chiral unsymmetrical dithioacetals involves acid-catalyzed reaction of aldehydes with a mixture of thiols of the formula HSR" and thioic S-acids of the formula $HSC(O)R^4$ to yield compounds of Formula C (as one component in a statistical distribution of components)

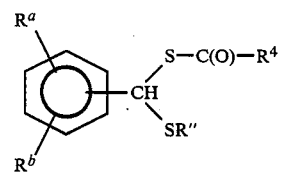

wherein $R^a$ and $R^b$ can be various substituents, including inter alia hydrogen and 2-substituted quinoline moieties; R" can be various substituents, including inter alia alkyl and carboxyalkyl; and $R^4$ can be chiral or achiral alkyl or optionally substituted aryl. Base hydrolysis of the S-acyl group of compounds of Formula C followed by alkylation of the resultant free thiol group yields dithioacetals of Formula D

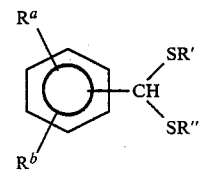

wherein $R^a$, $R^b$, R', and $R^4$ are defined as above and R' can be various substituents, including inter alia alkyl and carboxyalkyl. Although the method described in U.S. Ser. No. 011,166 can be used to prepare compounds described in the present invention, the methods are distinguishable by the differing reagents and conditions used and in the differing intermediates produced.

The present invention provides a particularly advantageous two-step method for preparing unsymmetrical dithioacetals and dithioketals from aryl aldehydes and ketones.

SUMMARY OF THE INVENTION

Applicants have discovered an advantageous process for preparing unsymmetrical dithioacetals and dithioketals of Formula I

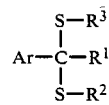

wherein Ar is:

(a)

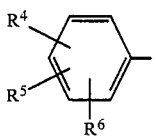

wherein
R[4] is:
(i) hydrogen;
(ii) $C_1$-$C_6$ alkyl;
(iii) $C_1$-$C_6$ alkoxy;
(iv) halogen;
(v) cyano;
(vi) nitro; or
(vii) formyl;
(viii) $C_2$-$C_6$ alkanoyl; or
(ix)

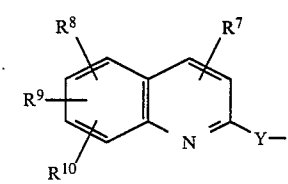

wherein
Y is:
(A) $C_2$-$C_6$ alkylene;
(B) $C_2$-$C_6$ alkenylene; or
(C) $C_2$-$C_6$ alkynylene; and
R[7], R[8], R[9], and R[10] are independently:
(A) hydrogen;
(B) $C_1$-$C_6$ alkyl;
(C) $C_1$-$C_6$ alkoxy;
(D) halogen;
(E) cyano; or
(F) nitro; and
R[5] and R[6] are independently:
(i) hydrogen;
(ii) $C_1$-$C_6$ alkyl;
(iii) $C_1$-$C_6$ alkoxy;
(iv) halogen;
(v) cyano;
(vi) nitro;
(vii) formyl; or
(viii) $C_2$-$C_6$ alkanoyl;
(b) aryl having 10 or 14 nuclear ring carbon atoms or said aryl substituted with one or more substituents selected from the group consisting of:
(i) $C_1$-$C_6$ alkyl;
(ii) $C_1$-$C_6$ alkoxy;
(iii) halogen;
(iv) cyano;
(v) nitro;
(vi) formyl; and
(vii) $C_2$-$C_6$ alkanoyl;
(c) heteroaryl having 5 or 6 nuclear ring atoms of which at least one nuclear ring atom is O, S, or N, or said heteroaryl substituted with one or more substituents selected from the group consisting of:
(i) $C_1$-$C_6$ alkyl;
(ii) $C_1$-$C_6$ alkoxy;
(iii) halogen;
(vi) cyano; and
(v) nitro;

R[1] is:
(a) hydrogen;
(b) $C_1$-$C_6$ alkyl;
(c) $C_2$-$C_6$ alkenyl;
(d) $C_3$-$C_7$ cycloalkyl;
(e) $C_4$-$C_{11}$ (cycloalkyl)alkyl; or
(f) $C_7$-$C_{14}$ aralkyl; and
R[2] and R[3] are independently:
(a) $C_1$-$C_6$ alkyl;
(b) $C_2$-$C_6$ alkenyl;
(c) $C_3$-$C_7$ cycloalkyl;
(d) $C_4$-$C_{11}$ (cycloalkyl)alkyl;
(e) $C_7$-$C_{14}$ aralkyl;
(f) —$(CH_2)_m$—(C=O)—$Z^1$,
wherein
$Z^1$ is:
(i) hydroxy;
(ii) $C_1$-$C_6$ alkoxy; or
(iii) $NR^{11}R^{12}$, wherein $R^{11}$ and $R^{12}$ are independently hydrogen or $C_1$-$C_6$ alkyl, or wherein $R^{11}$ and $R^{12}$ taken together are $C_2$-$C_6$ alkylene; and
m is an integer of from 1 to 10; or
(g) —$(CH_2)_n$—(C=O)—$Z^2$,
wherein
$Z^2$ is:
(i) hydroxy;
(ii) $C_1$-$C_6$ alkoxy; or
(iii) $NR^{13}R^{14}$, wherein $R^{13}$ and $R^{14}$ are independently hydrogen or $C_1$-$C_6$ alkyl, or wherein $R^{13}$ and $R^{14}$ taken together are $C_2$-$C_6$ alkylene; and
n is an integer of from 1 to 10.

In particular, applicants have discovered a novel process of preparing compounds of Formula I comprising:
(a) allowing one part by moles of a compound of the formula

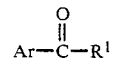

to react, in a suitable organic solvent, with a mixture of about 0.8 to 1.2 parts by moles of a thiol of the formula $R^2SH$ and an excess of a suitable hexaalkyldisilazane, in the presence of a suitable N-heterocycle catalyst, to form a trialkylsilylated hemithioacetal intermediate of the formula

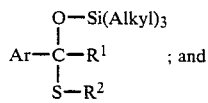 ; and (b) allowing the trialkylsilylated hemithioacetal intermediate to react, in a suitable organic solvent, with at least about 0.8 to 1.2 parts by moles of a thiol of the formula $R^3SH$, in the presence of a suitable Lewis acid.

The term "$C_1$-$C_6$ alkyl" refers to straight or branched chain aliphatic hydrocarbons having from 1 to 6 carbon atoms and is also referred to as lower alkyl. Examples of $C_1$-$C_6$ alkyl are methyl, ethyl, propyl, butyl, pentyl, hexyl, and the isomeric forms thereof. Similarly, the term "Alkyl" as used as a substituent of a silicon atom represents one or more independent $C_1$-$C_6$ alkyl groups.

The term "C$_1$–C$_6$ alkoxy" refers to straight or branched chain alkyl oxy groups having from 1 to 6 carbon atoms. Examples of C$_1$–C$_6$ alkoxy are methoxy, ethoxy, propoxy, butoxy, pentyloxy, hexyloxy, and isomeric forms thereof.

The term "C$_2$–C$_6$ alkanoyl" refers to straight or branched chain alkanoyl groups having from 2 to 6 carbon atoms. Examples of C$_2$–C$_6$ alkyl are acetyl, propanoyl, butanoyl, pentanoyl, hexanoyl, and the isomeric forms thereof.

The term "C$_2$–C$_6$ alkylene" refers to aliphatic hydrocarbon chains substituted at two different carbon atoms. Examples of C$_2$–C$_6$ alkylene are —(CH$_2$)$_2$—, —(CH$_2$)$_3$—, —(CH$_2$)$_4$—, —(CH$_2$)$_5$—, —(CH$_2$)$_6$—, and isomeric forms thereof. When used as ring-forming nitrogen substituents of Z$^1$ or Z$^2$, C$_2$–C$_6$ alkylene chains are taken with nitrogen atoms of NR$^{11}$R$^{12}$ or NR$^{13}$R$^{14}$ to form 1-azacycloalkyl groups: 1-azacyclopropyl, 1-azacyclobutyl, 1-azacyclopentyl, 1-azacyclohexyl, and 1-azacycloheptyl.

The term "C$_2$–C$_6$ alkenylene" refers to aliphatic hydrocarbon chains substituted at two different carbon atoms and containing one carbon-carbon double bond. Examples of C$_2$–C$_6$ alkylene are —CH=CH—, —CH=CHCH$_2$—, —CH$_2$CH=CH—, —CH=CHCH$_2$CH$_2$—, —CH$_2$CH=CHCH$_2$—, —CH$_2$CH$_2$CH=CH—, and the like, and isomeric forms thereof.

The term "C$_2$–C$_6$ alkynylene" refers to aliphatic hydrocarbon chains substituted at two different carbon atoms and containing one carbon-carbon triple bond. Examples of C$_2$–C$_6$ alkenylene are —C≡C—, —C≡CCH$_2$—, —CH$_2$C≡C—, —C≡CCH$_2$CH$_2$—, —CH$_2$C≡CCH$_2$—, —CH$_2$CH$_2$C≡C—, and the like, and isomeric forms thereof.

The term "aryl having 10 or 14 nuclear ring carbon atoms" refers to aromatic hydrocarbon substituents having two or three fused rings. Examples of such aryl groups include 1-naphthyl, 2-naphthyl, and various substituent groups derived from anthracene and phenanthrene.

The term "heteroaryl" refers to aromatic ring systems having 5 or 6 nuclear ring atoms, of which at least one nuclear ring atom is independently N, O, or S, and the rest are carbon. Examples of heteroaryl having 5 or 6 nuclear ring atoms include 1-, 2-, and 3-pyrrolyl; 1-, 2-, and 4-imidazolyl; 2- and 3-thienyl; 2- and 3-furanyl; 2-, 3-, and 4-pyridinyl; 2- and 4-pyrimidinyl; s-triazinyl; 3-, 4-, and 5-isoxazolyl; 3-, 4-, and 5-isothiazolyl; and other such groups known in the art.

The term "C$_3$–C$_6$ alkenyl" refers to straight or branched chain hydrocarbon groups having from 3 to 6 carbon atoms and possessing one carbon-carbon double bond. Examples of C$_3$–C$_6$ alkyl are allyl; 2- and 3-butenyl; 2-, 3-, and 4-pentyl; 2-, 3-, 4-, and 5-hexenyl; and the isomeric forms thereof.

The term "C$_3$–C$_7$ cycloalkyl" refers to saturated monocyclic hydrocarbon groups having from 3 to 7 carbon atoms in the ring. Examples of C$_3$–C$_7$ cycloalkyl are cyclopropyl, cyclobutyl, cyclopentyl, cyclohexyl, and cycloheptyl.

The term "C$_4$–C$_{11}$ (cycloalkyl)alkyl" refers to straight or branched chain alkyl groups bearing a cycloalkyl group such that the total number of carbon atoms ranges from 4 to 11. Examples of C$_4$–C$_{11}$ (cycloalkyl)alkyl are cyclopropylmethyl, cyclopropylethyl, cyclopropylpropyl, cyclobutylmethyl, cyclobutylethyl, cyclopentylmethyl, cyclopentylethyl, cyclohexylmethyl, cyclohexylethyl cycloheptylmethyl, cycloheptylethyl, and the like, and isomeric forms thereof.

The term "C$_7$–C$_{14}$ aralkyl" refers to straight or branched chain alkyl groups bearing a phenyl or naphthyl group such that the total number of carbon atoms ranges from 7 to 14. Examples of C$_7$–C$_{14}$ aralkyl are benzyl, phenethyl, phenylpropyl, (1-naphthyl)methyl, (2-naphthyl)methyl, (1-naphthyl)ethyl, (2-naphthyl)ethyl, and the like, and isomeric forms thereof.

Examples of halogen are fluorine, chlorine, bromine, and iodine.

DESCRIPTION OF THE INVENTION

The process of this invention may be effectuated by the general procedures illustrated in the following Scheme A. Unless otherwise specified, the various substituents are defined as for Formula I, above.

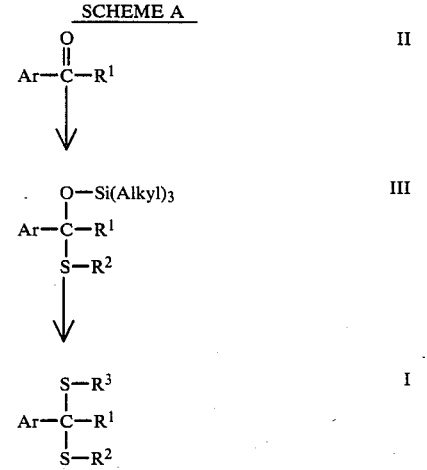

A trialkylsilylated hemithioacetal intermediate of Formula III can be formed by reaction, in a suitable organic solvent containing a suitable N-heterocycle catalyst, of an aldehyde or ketone of Formula II with about 0.8 to 1.2 parts by moles of a thiol of the formula R$^2$SH and an excess of a suitable hexaalkyldisilazane. As used in describing this reaction, the range of about 0.8 to 1.2 moles of the thiol per mole of the compound of Formula II reflects the desirability of minimizing the amount of unreacted compounds of Formula II caused by using insufficient amounts of thiol R$^2$SH while at the same time minimizing the amount of symmetrical dithioacetals and dithioketals caused by using excess thiol R$^2$SH. Thus, although the reaction to form trialkylsilylated hemithioacetal intermediates of Formula III will proceed over a broader reactant ratio, the preferred amount of a thiol of the formula R$^2$SH is approximately equimolar relative to aldehyde or ketone of Formula II.

Suitable hexaalkyldisilazanes are compounds of the formula (Alkyl)$_3$SiNHSi(Alkyl)$_3$ (wherein Alkyl represents one or more independent C$_1$–C$_6$ alkyl groups) that, in the presence of a suitable N-heterocycle, react readily with aldehydes and ketones of Formula II to form trialkylsilylated hemithioacetal intermediates of Formula III. Suitable hexaalkyldisilazanes are further characterized by the formation of trialkylsilyloxy groups that can be displaced readily from compounds of Formula III by a thiol of the formula R$^3$SH to form the dithioacetals and dithioketals of Formula I. Examples of hexaalkyldisilazanes include hexamethyldisilazane, hexaethyldisilazane, and the like, and isomeric forms thereof. A preferred hexaalkyldisilazane is hexamethyldisilazane. As used in describing this reaction, the term "excess hexaalkyldisilazane" encompasses the range of about 1 to 3 moles of the hexaalkyldisilazane per mole of the compound of Formula II. Although the reaction to form trialkylsilylated hemithioacetal intermediates of Formula III will proceed using greater quantities of hexaalkyldisilazane, such larger quantities are unnecessary and wasteful. A preferred quantity of hexamethyldisilazane is about 2 moles per mole of the compound of Formula II.

Suitable N-heterocycle catalysts are ring-nitrogen containing aromatic compounds that facilitate the formation of trialkylsilylated hemithioacetal intermediates of Formula III but which do not themselves form significant quantities of byproducts by reaction with other chemical reagents, intermediates, or reaction products. Examples of N-heterocycle catalysts include pyrrole; pyrazole; imidazole; pyrimidine; indole; indazole; and other such groups known in the art. A preferred N-heterocycle catalyst is imidazole.

The combination of a suitable hexaalkyldisilazane and a suitable N-heterocycle catalyst facilitates improved yields and purity of intermediates of Formula III and simplifies purification of the unsymmetrical dithioacetals and dithioketals of Formula I. For example, a combination of hexamethyldisilazane and imidazole produces cleanly the trimethylsilylated hemithioacetal intermediate illustrated in Example 3, below, whereas an approximately stoichiometric amount of the reagent trimethylsilylimidazole produces a byproduct (illustrated in Example 4, below) that reduces yields and complicates purification. One manner by which the byproduct illustrated in Example 4 can complicate purification is its ability to react in later steps in much the same way as would the corresponding aldehyde. That is, the byproduct can subsequently produce a statistical mixture of desired unsymmetrical dithioacetals and undesired symmetrical dithioacetals, thereby reducing the overall selectivity of the process.

Suitable organic solvents for the formation of trialkylsilylated hemithioacetal intermediates of Formula III are organic liquids in which the various reactants can be dissolved or suspended but which are otherwise chemically inert. Examples of suitable organic solvents inlcude alkanes and cycloalkanes; ethers and cyclic ethers, such as diethyl ether, tetrahydrofuran, tetrahydropyran, and dioxane; aromatic hydrocarbons, such as benzene, toluene, and xylene; halocarbons, such as chloroform, dichloromethane, and ethylene dichloride; cyanoalkanes, such as acetonitrile and propanenitrile; and other organic solvents known in the art. A preferred organic solvent is dichloromethane.

An unsymmetrical dithioacetal and dithioketal of Formula I can be formed by reaction, in a suitable organic solvent, of a trialkysilylated hemithioacetal intermediate of Formula III with at least about 0.8 to 1.2 parts by moles of thiol of the formula $R^3SH$ in the presence of a suitable Lewis acid. Suitable Lewis acids are electron-poor inorganic compounds, or dissociable complexes thereof, that facilitate the formation of compounds of Formula I but which do not themselves form significant quantities of byproducts by reaction with other chemical reagents, intermediates, or reaction products. Examples of suitable Lewis acids include boron trifluoride or boron trifluoride etherate, titanium tetrachloride, titanium tetraisopropoxide, aluminum trichloride, zinc chloride, and the like. A preferred Lewis acid is boron trifluoride etherate.

Suitable organic solvents for the conversion of compounds of Formula III to unsymmetrical dithioacetals and dithioketals of Formula I are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; alkanoate esters, such as ethyl acetate; aromatic hydrocarbons, such as benzene, toluene, and xylene; halocarbons, such as chloroform, dichloromethane, and ethylene dichloride; dialkyl carbonates and cyclic carbonates, such as diethyl carbonate and propylene carbonate; nitroalkanes, such as nitromethane; and other organic solvents known in the art. Preferred organic solvents inlcude dichloromethane, diethyl carbonate, propylene carbonate, and nitromethane.

The reactions of Scheme A may be run over a relatively broad temperature range, typically from about $-80°$ C. to about $80°$ C. A preferred temperature range is about $15°$ C. to about $30°$ C. for the first step and about $-50°$ C. to about $-10°$ C. for the second step.

The procedures shown in the following Scheme B illustrate a more specific embodiment of this invention. Unless otherwise specified, the various substituents are defined as for Formula I, above.

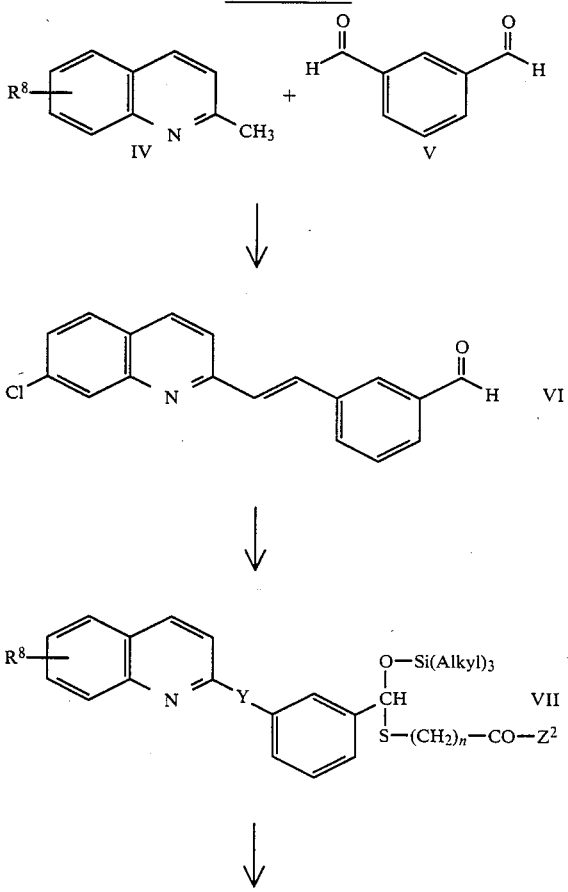

SCHEME B

-continued
SCHEME B

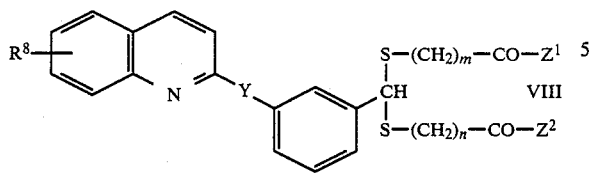

An aldehyde of Formula VI may be prepared by any of several methods known in the art. For example, a preferred method involves condensation of compounds of Formulas IV and V using as a condensation medium any of several condensing agents known in the art, such as an acid anhydride, in a heated organic solvent. A preferred condensation medium is acetic anhydride in refluxing xylene.

Using the methods described above for preparing compounds of Formula III (see Scheme A), an aldehyde of Formula VI can be converted by reaction with a thiol of the formula HS—$(CH_2)_n$—(C=O)—$Z^2$ to a trialkylsilylated hemithioacetal intermediate of Formula VII wherein Y is —CH=CH—.

Using the methods described above for preparing compounds of Formula I (see Scheme A), a trialkylsilylated hemithioacetal intermediate of Formula VII can be converted by reaction with a thiol of the formula HS—$(CH_2)_m$—(C=O)—$Z^1$ to an unsymmetrical dithioacetal of Formula VIII wherein Y is —CH=CH—.

If desired, the bridging alkenylene group —CH=CH— of a compound of Formula VI can be converted to the corresponding alkylene group —$CH_2CH_2$— by selective reduction of the double bond using methods known in the art. The alkylene analogs of compounds VII and VIII in which Y is —$CH_2CH_2$— can then be prepared as above using the alkylene analog of compound VI in place of compound VI itself.

Where $Z^1$ and $Z^2$ form ester groups, hydrolysis to the free carboxylic acid functions can be effected using methods known in the art.

The procedures shown in the following Scheme C illustrate an alternative specific embodiment of this invention. Unless otherwise specified, the various substituents are defined as for Formula I, above.

SCHEME C

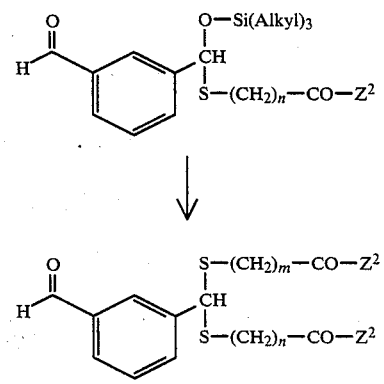

-continued
SCHEME C

Using the methods described above for preparing compounds of Formula III (see Scheme A), an aldehyde of Formula V can be converted by reaction with a thiol of the formula HS—$(CH_2)_n$—(C=O)—$Z^2$ to a trialkylsilylated hemithioacetal benzaldehyde intermediate of Formula IX.

Using the methods described above for preparing compounds of Formula I (see Scheme A), a trialkylsilylated hemithioacetal benzaldehyde intermediate of Formula IX can be converted by reaction with a thiol of the formula HS—$(CH_2)_m$—(C=O)—$Z^1$ to an unsymmetrical dithioacetal benzaldehyde of Formula X.

Using the methods described above for preparing compounds of Formula VI (see Scheme B), an unsymmetrical dithioacetal benzaldehyde of Formula X can be converted to compounds of Formula VIII wherein Y is —CH=CH—. If desired, the bridging alkenylene group —CH=CH— of a compound of Formula X can be converted to the corresponding alkylene group —$CH_2CH_2$— by selective reduction of the double bond using methods known in the art.

The preferred embodiments of this invention include a process for preparing compounds of the following general formula

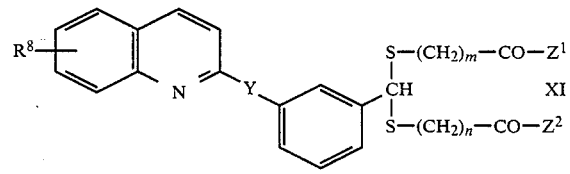

wherein
$R^8$ is:
(a) hydrogen;
(b) $C_1$-$C_6$ alkyl;
(c) $C_1$-$C_6$ alkoxy; or
(d) halogen;
Y is:
(a) $C_2$-$C_6$ alkylene; or
(b) $C_2$-$C_6$ alkenylene;
$Z^1$ is $C_1$-$C_6$ alkoxy or $NR^{11}R^{12}$, wherein
  $R^{11}$ and $R^{12}$ are independently hydrogen or $C_1$-$C_6$ alkyl;
$Z^2$ is $C_1$-$C_6$ alkoxy or $NR^{13}R^{14}$, wherein
  $R^{13}$ and $R^{14}$ are independently hydrogen or $C_1$-$C_6$ alkyl; and
m and n are independently integers of from 1 to 4;
comprising:
  (a) allowing one part by moles of a compound of the formula

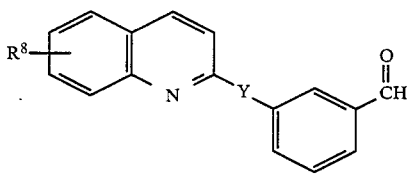

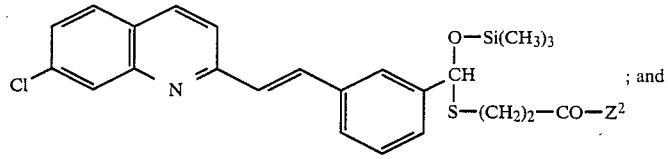

to react, in a suitable organic solvent, with a mixture of about 0.8 to 1.2 parts by moles of a thiol of the formula HS—(CH$_2$)$_n$—(C=O)—Z$^2$ and an excess of hexamethyldisilazane, in the presence of imidazole, to form a trimethylsilylated hemithioacetal intermediate of the formula

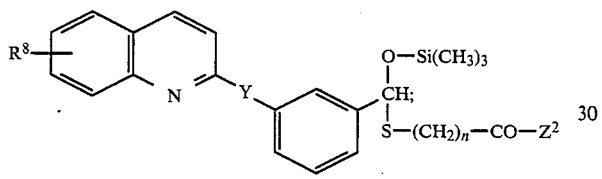

and (b) allowing the trimethylsilylated hemithioacetal intermediate to react, in a suitable organic solvent, with at least about 0.8 to 1.2 parts by moles of a thiol of the formula HS—(CH$_2$)$_m$—(C=O)—Z$^1$, in the presence of boron trifluoride etherate.

The most preferred embodiments of this invention include a process for preparing compounds of the following formula

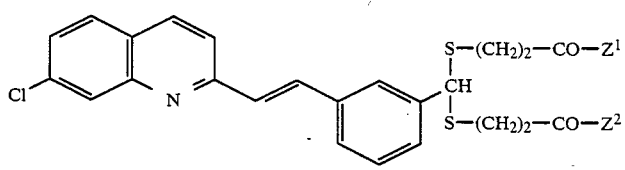

wherein Z$^1$ is C$_1$–C$_6$ alkoxy and Z$^2$ is NR$^{13}$R$^{14}$ (wherein R$^{13}$ and R$^{14}$ are independently C$_1$–C$_6$ alkyl), or Z$^1$ is NR$^{11}$R$^{12}$ (wherein R$^{11}$ and R$^{12}$ are independently C$_1$–C$_6$ alkyl) and Z$^2$ is C$_1$–C$_6$ alkoxy; comprising:

(a) allowing a compound of the formula

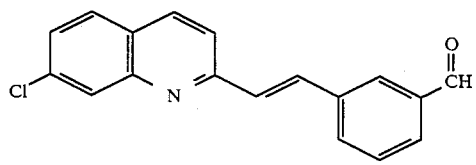

to react, in a suitable organic solvent, with a mixture of about 0.8 to 1.2 parts by moles of a thiol of the formula HS—(CH$_2$)$_2$—(C=O)—Z$^2$ and an excess of hexamethyldisilazane, in the presence of imidazole, to form a trimethylsilylated hemithioacetal intermediate of the formula

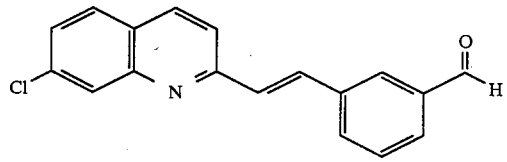

; and (b) allowing the trimethylsilylated hemithioacetal intermediate to react, in a suitable organic solvent, with at least about 0.8 to 1.2 parts by moles of a thiol of the formula HS—(CH$_2$)$_2$—(C=O)—Z$^1$, in the presence of boron trifluoride etherate.

The following examples further illustrate details for the process of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

DESCRIPTION OF THE PREFERRED EMBODIMENTS

EXAMPLE 1

3-[2-(7-Chloro-2-quinolinyl)ethenyl]benzaldehyde

XII

To 15 liters of xylene preheated to 100° were added sequentially 7-chloroquinaldine (3 kg, 16.9 moles; see C. M. Leir, *J. Org. Chem.*, 42, 911–913 (1977)), isophthalaldehyde (3.4 kg, 25.3 moles), and acetic anhydride (4.69 liters, 5.07 kg, 49.7 moles). The mixture was heated at reflux for about 8 to 9 hours and then cooled to room temperature. Hexane (16 liters) was added and the resultant precipitate was collected by filtration. Recrystallization from ethyl acetate yielded pure title compound (67%).

EXAMPLE 2

3-Mercapto-N,N-dimethylpropanamide

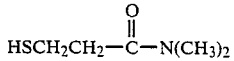

To N,N-dimethylacrylamide (1.24 liters, 1.19 kg, ca. 12 moles) cooled to about 0° under nitrogen was added over a period of two hours thioacetic acid (0.85 liters, 915 g, ca. 12 moles). After the mixture was allowed to stand at room temperature for at least four hours, methanol (6 liters) was added and the solution was cooled to about 0°. Aqueous 3N sodium hydroxide (6 liters) was added as temperature was maintained at 15°-20°. The mixture was then stirred at about 20° for two hours, cooled to about 0°, and neutralized (to pH 7.5) by addition of aqueous 12N hydrochloric acid as temperature was maintained at 15°-20°. The mixture was concentrated in vacuo to remove methanol, and the aqueous concentrate was extracted with dichloromethane (four 4-liter batches). The organic extract was washed with saturated aqueous sodium chloride (2 liters), dried over magnesium sulfate, filtered, and concentrated in vacuo to an oil. Vacuum distillation (95°-100° at 2 mm Hg) produced 1282 g (80.2%) of the title compound.

EXAMPLE 3

3-[[[3-[2-(7-Chloro-2-quinolinyl)ethenyl]phenyl][(trimethylsilyl)oxy]methyl]thio]-N,N-dimethylpropanamide

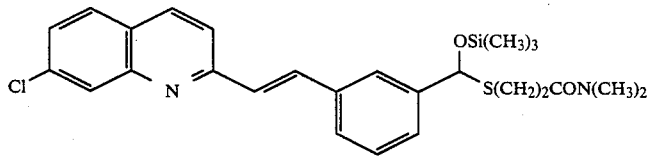

To a suspension of 3-[2-(7-chloroquinolin-2-yl)ethenyl]benzaldehyde (2.94 g, 10 mmole; see Example 1) in 20 ml of dichloromethane under a nitrogen atmosphere was added imidazole (136 mg, 2 mmole) and 3-mercapto-N,N-dimethylpropanamide (1.38 ml, 1.47 g, 11 mmole; see Example 2). Hexamethyldisilazane (4.22 ml, 3.23 g, 20 mmole) was then added rapidly with stirring. After 3 hours an additional 10 ml of dichloromethane was added and stirring was continued for an additional 40 hours. Trace solids were removed by filtration and the filtrate was concentrated in vacuo to an oil. Overnight drying under vacuum yielded the title compound as a viscous oil, which nmr spectroscopy indicated contained no unreacted aldehyde. The oily title compound was used in subsequent reactions without further purification.

EXAMPLE 4

3-[[[3-[2-(7-Chloro-2-quinolinyl)ethenyl]phenyl][(trimethylsilyl)oxy]methyl]thio]-N,N-dimethylpropanamide Alternative Method To a mixture of 3-[2-(7-chloroquinolin-2-yl)ethenyl]benzaldehyde 16.8 mg; see Example 1) and 3-mercapto-N,N-dimethylpropanamide (8.6 μl) in CD$_2$Cl$_2$ (in an nmr spectroscopy tube) was added trimethylsilylimidazole (11 μl). After 2½ hours nmr spectroscopy indicated a mixture of unreacted 3-mercapto-N,N-dimethylpropanamide, the 3-[[[3-[2-(7-chloro-2-quinolinyl)ethenyl]phenyl][(trimethylsilyl)oxy]methyl]thio]-N,N-dimethylpropanamide, and an imidazole adduct having the following formula:

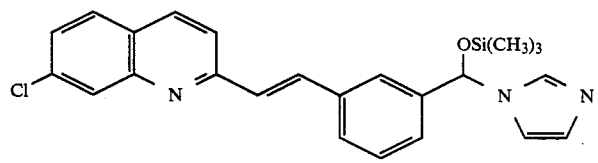

Products were not isolated from the reaction mixture.

EXAMPLE 5

Methyl 5-[3-[2-(7-chloro-2-quinolinyl)ethenyl]phenyl]-8-dimethylcarbamyl-4,6-dithiaoctanoate

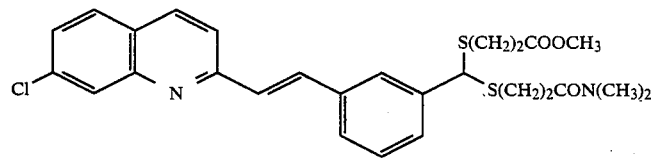

To a cold (ca. −40°) solution of 3-[[[3-[2-(7-chloro-2-quinolinyl)ethenyl]phenyl][(trimethylsilyl)oxy]methyl]thio]-N,N-dimethylpropanamide (see Example 3) in 40 ml of dichloromethane was added methyl 3-mercaptopropanoate (1.1 ml, 1.20 g, 10 mmole), followed by boron trifluoride etherate (3.7 ml, 4.26 g, 30 mmole). After ca. 7½ hours at ≦ −40° the reaction was allowed to warm to ca. −20° and diluted with 10 ml of dichloromethane. After about 15 minutes the reaction was quenched with 10% aqueous sodium carbonate (125 ml) and further diluted with 100 ml of dichloromethane. The organic layer was separated, then washed sequentially with aqueous sodium carbonate, water, and brine. The organic layer was again separated, dried over anhydrous potassium carbonate, filtered, and concentrated in vacuo. As determined by $^1$H nmr spectroscopy and high performance reverse phase chromatography, the resultant crude product contained a 78% yield of a highly selective mixture of the unsymmetrical title compound (14 molar parts), the corresponding symmetrical diester compound (1 molar part), and the corresponding symmetrical diamide compound (1 molar part). Chromatrography of the crude product on silica gel and crystallization from ethyl acetate-hexanes afforded the title compound, m.p. 108-109°. Structure assignment was confirmed by nmr spectroscopy.

$^1$H nmr (CDCl$_3$): δ (ppm) 2.55 (4H, m); 2.85 (4H, m); 2.91 (6H, br s); 3.67 (3H, s); 5.06 (1H, s); 7.35-8.16 (11H, m).

EXAMPLE 6

Methyl 5-[3-[2-(7-chloro-2-quinolinyl)ethenyl]phenyl]-8-dimethylcarbamyl-4,6-dithiaoctanoate Alternative Methods The title compound was prepared in various solvents by the general method of Example 5 using the following modifications.

To a cold (ca. −40°) solution of 3-[[[3-[2-(7-chloro-2-quinolinyl)ethenyl]phenyl][(trimethylsilyl)oxy]methyl]thio]-N,N-dimethylpropanamide (0.31 mmole; see Example 3) in 2.0 ml of the appropriate solvent was added methyl 3-mercaptopropanoate (40 μl, 0.35 mmole), followed by boron trifluoride etherate (0.15 ml, 1.2 mmole). After two hours at −40° the reaction was quenched with 10% aqueous sodium carbonate (10 ml) and further diluted with 10 ml of ethyl acetate. The organic layer was separated, then washed sequentially with water and brine. The organic layer was again separated, dried over anhydrous sodium sulfate, filtered, and concentrated in vacuo. As determined by $^1$H nmr spectroscopy and high performance reverse phase chromatography, the resultant crude product contained a highly selective mixture of the unsymmetrical title compound, the corresponding symmetrical diester compound, and the corresponding symmetrical diamide compound. The following Table I provides yields and product ratios for each solvent used.

TABLE I

| Solvent | Yield | Title compound:diester:diamide molar ratio |
| --- | --- | --- |
| Diethyl carbonate | 75% | 12:1:1 |
| Propylene carbonate | 75% | 10:1:1 |
| Nitromethane | 85% | 8:1:1 |

What is claimed is:

1. A process for preparing a compound having the formula

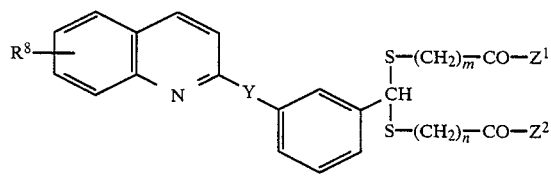

wherein
R$^8$ is:
(a) hydrogen;
(b) C$_1$-C$_6$ alkyl;
(c) C$_1$-C$_6$ alkoxy; or
(d) halogen;
Y is:
(a) C$_2$-C$_6$ alkylene; or
(b) C$_2$-C$_6$ alkenylene;
Z$^1$ is C$_1$-C$_6$ alkoxy or NR$^{11}$R$^{12}$, wherein
R$^{11}$ and R$^{12}$ are independently hydrogen or C$_1$-C$_6$ alkyl;
Z$^2$ is C$_1$-C$_6$ alkyl; and
m and n are independently integers of from 1 to 10;
comprising:
(a) allowing one part by moles of a compound of the formula

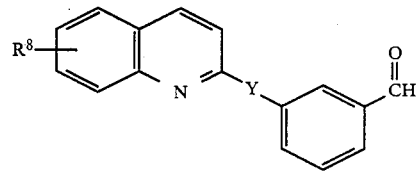

to react, in a suitable organic solvent, with a mixture of about 0.8 to 1.2 parts by moles of a thiol of the formula HS—(CH$_2$)$_n$—(C=O)—Z$^2$ and an excess of hexamethyldisilazane, in the presence of imidazole, to form a trimethylsilylated hemithioacetal intermediate of the formula

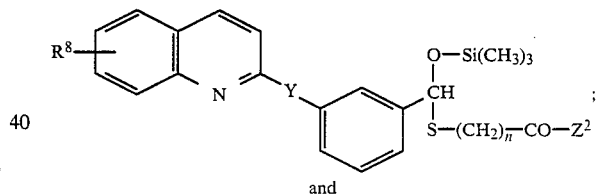

and (b) allowing the trimethylsilylated hemithioacetal intermediate to react, in a suitable organic solvent, with at least about 0.8 to 1.2 parts by moles of thiol of the formula HS—(CH$_2$)$_m$—(C=O)—Z$^1$, in the presence of boron trifluoride etherate.

2. A process according to claim 1 for preparing a compound having the formula

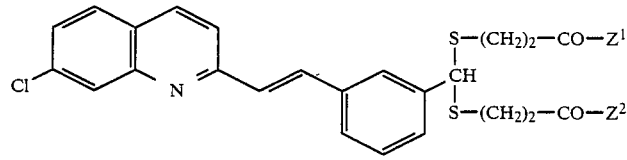

wherein
Z$^1$ is C$_1$-C$_6$ alkoxy or NR$^{11}$R$^{12}$,
wherein R$^{11}$ and R$^{12}$ are independently hydrogen or C$_1$-C$_6$ alkyl; and
Z$^2$ is C$_1$-C$_6$ alkoxy or NR$^{13}$R$^{14}$, wherein $R^{13}$ and $R^{14}$ are independently hydrogen or $C_1$–$C_6$ alkyl;

comprising:

(a) allowing one part by moles of a compound of the formula

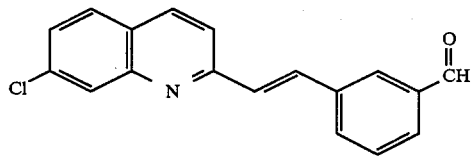

to react, in a suitable organic solvent, with a mixture of about 0.8 to 1.2 parts by moles of a thiol of the formula HS—$(CH_2)_2$—(C=O)—$Z^2$ and an excess of hexamethyldisilazane, in the presence of imidazole, to form a trimethylsilylated hemithioacetal intermediate of the formula

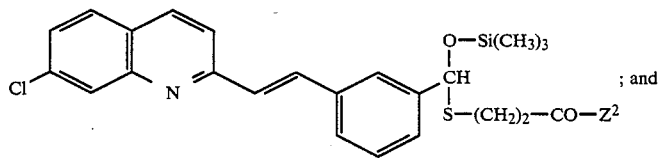

; and (b) allowing the trimethylsilylated hemithioacetal intermediate to react, in a suitable organic solvent, with at least about 0.8 to 1.2 parts by moles of a thiol of the formula HS—$(CH_2)_2$—(C=O)—$Z^1$, in the presence of boron trifluoride etherate.

3. A process according to claim 2 wherein $Z^1$ is $C_1$–$C_6$ alkoxy and $Z^2$ is $NR^{13}R^{14}$, wherein $R^{13}$ and $R^{14}$ are independently hydrogen or $C_1$–$C_6$ alkyl.

4. A process according to claim 2 wherein $Z^1$ is methoxy and $Z^2$ is $N(CH_3)_2$.

5. A process according to claim 4 wherein the organic solvent is dichloromethane, diethyl carbonate, propylene carbonate, or nitromethane.

6. A process according to claim 5 for preparing methyl 5-[3-[2-(7-chloro-2-quinolinyl)ethyl]phenyl]-8-dimethylcarbamyl-4,6-dithiaoctanoate, having the formula

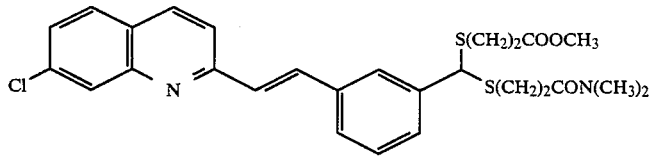

comprising:

(a) allowing one part by moles of a compound of the formula

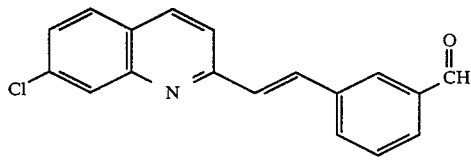

to react, in dichloromethane, with a mixture of about 0.8 to 1.2 parts by moles of HS—$(CH_2)_2$—$CON(CH_3)_2$ and an excess of hexamethyldisilazane, in the presence of imidazole, to form a trimethylsilylated hemithioacetal intermediate of the formula

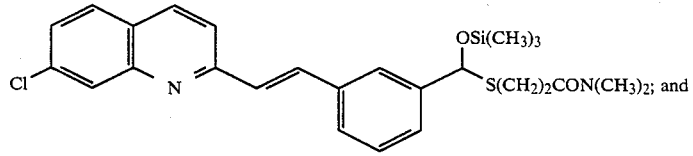

(b) allowing the trimethylsilated hemithioacetal intermediate to react, in dichloromethane, diethyl carbonate, propylene carbonate, or nitromethane, with at least about 0.8 to 1.2 parts by moles of HS—$(CH_2)_2$—$COOCH_3$, in the presence of boron trifluoride etherate.

* * * * *